| United States Patent [19] | [11] Patent Number: 4,867,796 |
| Asmus et al. | [45] Date of Patent: Sep. 19, 1989 |

[54] PHOTODECONTAMINATION OF SURFACES

[75] Inventors: John Asmus, La Jolla, Calif.; Keith Boyer, Los Alamos, N. Mex.

[73] Assignee: Maxwell Laboratories, Inc., San Diego, Calif.

[21] Appl. No.: 96,064

[22] Filed: Sep. 8, 1987

Related U.S. Application Data

[63] Continuation-in-part of Ser. No. 930,646, Nov. 13, 1986, abandoned, and a continuation of Ser. No. 703,289, Feb. 20, 1985, abandoned, which is a continuation-in-part of Ser. No. 365,247, Apr. 5, 1982, abandoned.

[51] Int. Cl.$^4$ ................................................ B08B 7/00
[52] U.S. Cl. ........................................................ 131/1
[58] Field of Search ............................................ 134/1

[56] References Cited

FOREIGN PATENT DOCUMENTS 0119181  9/1980  Japan ........................................ 134/1

OTHER PUBLICATIONS

Brannon, "Citric Acid Augmented Flashlamp Cleaning of Corroded Steel Surfaces", Applic. of Surf. Sci (9), pp. 14–21, 1981.

*Primary Examiner*—Ferris H. Lander
*Attorney, Agent, or Firm*—Fitch, Even, Tabin & Flannery

[57] ABSTRACT

As a method of decontaminating a surface covered with a chemical contaminant, a light-absorption agent providing a relatively high neutral density is applied to the surface in intimate contact with the contaminant. Then one or more flashes of high intensity, broad-band frequency, incoherent light is applied to the surface, whereupon, the light-absorption agent converts the absorbed light energy to heat, resulting in vaporization and/or decomposition of the contaminant. The heat generated by the short duration flash is localized at the material on the surface and at a very thin surface layer, and vaporization of the surface material dissipates the heat that is generated, whereby, the surface is substantially unaffected by the process.

11 Claims, No Drawings

PHOTODECONTAMINATION OF SURFACES

This application is a continuation-in-part of application Ser. No. 930,646, now abandoned, filed Nov. 13, 1986 and a continuation of application Ser. No. 703,289, filed Feb. 20, 1985, now abandoned, which is a continuation-in-part of application Ser. No. 365,247, filed Apr. 5, 1982, abandoned.

The present invention relates to a method of surface decontamination and more particularly to the removal of hazardous chemicals from surfaces using broad-band frequency, high intensity light pulses.

BACKGROUND OF THE INVENTION

There are instances where large surfaces may become contaminated with various hazardous materials. For example, international hostilities or terrorist activities may provoke the dispersion of a chemical warfare agent over a broad area, covering a variety of surfaces. Other examples are industrial or transportation accidents in which a hazardous chemical may be spilled or leaked. A number of chemical substances which might be dispersed in such situations are very hazardous, and at the present time, there is no efficient means to remove such chemical substances from certain surfaces by conventional means. An attempt to remove such chemicals by washing would be relatively slow, provide little assurance of substantially complete removal, would spread the chemicals to other areas, e.g., through the washing solutions, and would pose a serious health hazard to workers removing the chemicals.

The present invention provides a method of photometrically removing contaminants from surfaces using apparatus that is readily transportable to the site where decontamination of surfaces is needed and which not only removes hazardous chemicals from surfaces, but substantially decomposes many such chemicals during removal. Decontamination by the method of the present invention is easily controllable, allowing chemicals to be removed from the surface without significant damage to the surface itself.

More specifically, the invention provides for removal of surface contaminants by exposure of a contaminated surface to pulses of high-intensity, polychromatic, incoherent light radiation, such as is provided by powerful xenon flashlamps, e.g., those sold under the tradename "Flashblast" by Maxwell Laboratories, Inc. It is known to remove materials from surfaces using pulses of such radiation. For example, removal of barnacles, etc. from the metal hulls of ships using high-intensity flashlamp radiation is described in T. Johnson, *Popular Science* (1982) pp. 82-84.

It is found, however, that merely applying flashlamp radiation to a surface that is contaminated with a thin film or layer of hazardous contaminant does not provide satisfactory removal of the contaminant. If the contaminant and the surface are each non-absorbing of broad-band frequently light, e.g., a colorless contaminant on a glass or clear plastic surface, there will be insufficient heat generated in the region of the surface to vaporize and/or decompose the contaminant. If a contaminant that is substantially non-absorbing of light covers a light-absorbing surface, the surface will absorb the major portion of the radiation, and the surface may be marred by the heat generated at the surface. Furthermore, if the heating takes place primarily at the surface itself, there is a tendency for any surface contaminant layer to be dispersed from the surface in droplets, in which case, the surface tends to become recontaminated by the droplets as they settle thereon. If contaminants are to be permanently removed from surfaces, therefore, it is desirable to preferentially heat the contaminant relative to the surface.

Japanese Pat. No. 119,181 to Nippon Steel Corp. describes a method of removing rolling lubricant from steel plates. An IR-absorbing chemical is admixed with the lubricant that is applied to the steel as it is rolled. Subsequently, the surfaces of the steel plate are exposed to $CO_2$ laser radiation which is substantially monochromatic light in the infrared (IR) frequency range, the IR-absorbing chemical heating to a temperature whereat the chemical and the lubricant are removed from the surface. While this system is applicable to a process where chemicals are removed at a fixed location, e.g., at a certain step in a steel rolling process, it is generally impractical for decontaminating surfaces at locations, however remote, where contaminated surfaces might be found. $CO_2$ laser apparatus is expensive, delicate and difficult to transport, and would therefore be difficult to bring to the site where decontamination apparatus is needed. Furthermore, the combination of IR-absorbing chemicals with an IR-light source, is generally inapplicable to contaminant removal with pulsed broad-band radiation. Broad-band light that is weighted to IR frequencies may be produced by flashlamps in conjunction with a suitable window or lens material; however, due to internal heating problems, broad-band frequency light, heavily weighted to the IR frequencies can only be produced of relatively low power which is insufficient for vaporization and/or decomposition of surface contaminants.

SUMMARY OF THE INVENTION

The invention provides a method of removing a chemical contaminant from a surface. The chemical contaminant is intimately contacted with a light-absorption agent which absorbs broad-band frequency light radiation. Then, the surface is exposed to one or more pulses of intense, broad-band frequency, incoherent light radiation, each pulse being delivered in about 10 milliseconds or less. Absorption of the radiation by the light-absorption agent results in the generation of heat localized in a very thin layer which vaporizes and/or decomposes the contaminant on the surface. The distribution of absorption coefficients of the light-absorption agent is matched to the frequency or wavelength distribution of the pulsed light radiation, which is preferably predominantly in the visible spectrum. The absorption agent is applied to the surface, either subsequent to contamination or as an additive to the contaminant in anticipation of it contaminating surfaces, in amounts to deliver a neutral density of at least about 0.3, and the pulses have sufficient intensity to provide at least about 6 joules per $cm^2$ of surface area.

DETAILED DESCRIPTION OF PREFERRED EMBODIMENTS

In accordance with the present invention, a light-absorption agent is applied to a surface that is covered with a chemical contaminant, and one or more short pulses or flashes of broad-band frequency, incoherent light radiation is applied to the surface, whereupon the light-absorption agent absorbs the light, and heats up, resulting in vaporization and/or decomposition of the contaminant with which the light-absorption agent is in intimate contact. The frequency of the radiation emitted by the pulsed light source may extend across the light spectrum, through the ultraviolet (UV), the visible and the infrared (IR), i.e., electromagnetic wavelengths from 200 nm to 1000 nm, and the light-absorbing characteristics of the agent applied to the surface is generally matched to the spectrum emitted by the pulsed light source so that a substantial portion of the incident light is absorbed by the chemical.

Practical considerations indicate the preferred use of broad-band radiation weighted to the visible light spectrum, which herein refers to light having wavelengths between 380 and 720 nm and the use of a light-absorption agent having a distribution of absorption coefficients generally matched to the broad-band spectrum. The light-absorption agent is matched in absorption coefficient distribution and applied in a quantity per surface area so that it has a neutral density of at least about 0.3; that is, so that the agent absorbs at least about 50% of the energy of the pulsed incident light. It is found that it is necessary that the intensity of the light pulse and the proximity of the light source to the surface be such that at least about 6 joules per $cm^2$ and preferably about 10 joules per $cm^2$ are delivered to the surface by each pulse of radiation. Upon application of such a pulse or pulses of broad-band frequency light, the light-absorption agent absorbs sufficient energy to raise the temperature of materials on the surface to upwards of 1000° C., whereat vaporization and/or decomposition of materials on the surface, including the contaminant, result. Vaporization of the surface material removes heat from the surfaces, and a wide variety of surfaces can be treated without significantly affecting the surface itself. By applying light radiation in short duration pulses, the degree of surface treatment may be carefully controlled, whereby a surface may be decontaminated while surface deterioration is avoided or minimized. For decontamination purposes, there is generally little advantage to providing more than about 20 joules per $cm^2$ of surface area, and higher intensities tend to overheat and deteriorate the surfaces.

The decontamination method of the present invention is useful for decontaminating a wide variety of surfaces. The method, however, is primarily a thermal effect localized at a surface, and contaminants absorbed within an absorbent material will be relatively unaffected by treatment. Therefore, the method is most applicable to surfaces that do not absorb the contaminant. The application of the light-absorption agent to the contaminated surface is particularly advantageous with respect to surfaces which would otherwise tend to overheat and deteriorate upon exposure to the intense pulsed light radiation. The light-absorption agent absorbs a substantial amount of the incident radiation, preferably at least about 50 percent of the light energy, thereby shielding the surface itself from some of the radiation and its heating effects. Furthermore, vaporization of the materials and/or their decomposition products from the surface carries heat away from the surface.

The process, which includes the application of the light-absorption agent or dye to the surface, also provides important advantages with respect to removing contaminants from surfaces for which overheating is not a problem. It is found that when a contaminant covers a surface, and a pulse of radiation is applied to the surface without application of a light-absorption agent, the heating which occurs at the surface itself tends to disperse a substantial portion of the contaminant as droplets, rather than as vapor. Subsequently, a significant portion of the contaminant droplets tend to resettle on the surface. By application of the light-absorption agent in intimate contact with the surface contaminant, vaporization and/or decomposition of the contaminant is realized to a significantly greater degree.

The method of the present invention is applicable to removal of a variety of contaminants, particularly organic contaminants. At the localized temperatures produced by absorption of the intense radiation by the light-absorbing chemicals, most organic chemicals, such as those used as chemical warfare agents or as pesticides, will vaporize and/or decompose. It is found that the method of the present invention has similar decontaminating effects with respect to a wide variety of organic chemicals.

The vast majority of chemicals which would represent a serious hazard, such as chemical warfare agents or pesticides, do not in themselves absorb substantial amounts of broad-band frequency light radiation, thus requiring the addition of the light-absorption agent for generating sufficient heat to vaporize or decompose the same. Even a chemical contaminant which might be relatively colored and therefore sufficiently light-absorbing to be vaporized and/or decomposed by intense broad-band light radiation may be hazardous when present on a surface at a very low level. Accordingly, a light-absorbing chemical is preferably added even with such a contaminant so that the radiation is absorbed primarily by the materials on the surface, rather than by the surface itself.

The preferred radiation source is a flashlamp, such as described above. Flashlamps deliver very high intensity pulses over very brief periods of time and therefore deliver their energy to a light-absorption agent on a surface substantially instantaneously, without heat having time to dissipate inward. Accordingly, heat is generated substantially entirely in the material and in a very thin layer of the surface. Typically, the discharge of a flashlamp is about 1 millisecond, although the discharge period may range up to about 10 milliseconds. A discharge of more than about 10 milliseconds will shift the discharge spectrum to the infrared, resulting in a low power output that is insufficient to produce the desired thermal decontaminating effect. The pulse may be as short as can be produced by a flashlamp, shorter pulses tending to localize heat at a very thin surface layer. However, shorter pulses also tend to produce localized heating in the flashlamp itself, and at the present time, it is preferred that the discharge time be at least about 0.1 millisecond to promote longer life of the flashlamp head.

Flashlamps or gaseous discharge lamps are advantageous for decontaminating surfaces in locations wherever contamination may exist. A flashlamp apparatus includes a power supply and associated circuitry as well as flashlamp heads which contain the gaseous discharge lamps themselves and appropriate reflectors for directing the emitted energy at the surface. As flashlamps for decontamination purposes require substantial power, the power supplies may be relatively heavy, but may nevertheless be easily transported on a variety of vehicles to a decontamination site. The heads themselves are lightweight, typically weighing a few pounds, and may be connected to the power supply by flexible cables and easily carried by an operator and positioned closely adjacent to the contaminated surface. This feature is particularly important when an irregular surface is being decontaminated as it allows the operator to reposition the flashlamp against surfaces of a contaminated object according to its contours. It is important that an operator be able to move the head of the flashlamp closely adjacent to surfaces of the object because the flashlamp radiation is subject to the inverse square law which makes it imperative that the flashlamp head be close enough to the surface to deliver the requisite thermal power. Flashlamps can be used to decontaminate large surface areas. A portable head, for example may easily decontaminate 0.1–1.0 $m^2$ of surface area in a single position relative to the surface. By repeatedly repositioning the head, an entire large surface area may be decontaminated relatively quickly.

For decontamination situations where several pulses are desirably administered, the pulses may be repeated as rapidly as is consistent with the flash apparatus. At the present time, flashlamps are available which generate the high intensity pulses at the rate of about 4 times per second, and many decontamination applications require less than 4 pulses. On the other hand, it may be desirable to space the pulses apart by several seconds to permit monitoring of decontamination and surface effects between pulses.

An advantage of supplying the energy by pulsed radiation rather than by continuous radiation is that it permits much better control of decontamination conditions, allowing the surface to be decontaminated while at the same time monitoring the surface to assure that surface changes are minimized. Subsequent to a flash of radiation, a haze develops adjacent to the surface as a result of the vaporization and decomposition of the materials from the surface. If pulses are spaced sufficiently to allow the haze to dissipate, the surface may be observed, either with the naked eye or with instrumentation to check whether the surface is being altered. The application of a visible dye or dyes as the light-absorption agent facilitates monitoring of surface decontamination, as removal of the colored agent is a good indication of effective decontamination. In contrast, examination of a surface being subjected to continuous light radiation would be continuously obscured by the haze that is produced, enhancing the likelihood of the surface being over-exposed or under-exposed.

It is preferred that the broad-band frequency radiation be delivered predominantly in the visible frequency, e.g., greater than about 50% of the light energy being in the visible spectrum and more preferably greater than about 70% of the light energy being in the visible spectrum; however, all light frequencies are acceptable, provided that the frequencies can be delivered with sufficient intensity to a light-absorbing chemical of matched extinction coefficient distribution. As noted above, it is difficult to provide pulsed infrared radiation of sufficient intensity for purposes of this invention. Pulsed radiation weighted to the UV frequencies may be produced of sufficient intensity, but the plasma temperatures produced in the discharge gas in the lamp are hotter, and lamps weighted toward the UV have shorter lives. The decontamination is found to be substantially entirely a thermal effect and not a photochemical effect. Thus, there appears to be little advantage to a frequency distribution weighted toward the more photochemically active UV frequencies, at least not relative to the practical advantages which accrue through use of light weighted to the visible frequencies.

Preferably, xenon flashlamps are used to produce the pulsed radiation discharge because xenon flashlamps produce broad-band spectra and are relatively cool. Nitrogen or argon flashlamps might also be used, but these are hotter lamps and have shorter lives. The lens or window of the lamp is selected to transmit as much as possible of the light produced by the discharge. Preferably, a fused silica (synthetic quartz) window is used, as it transmits through the visible frequencies and well into the UV range. However, an ordinary glass window is suitable which is transparent throughout the visible range.

The light-absorption agent should have a distribution of absorption coefficients generally matched to that of the lamp-discharged radiation so as to absorb as much of the transmitted light as possible and should be applied to the surface to provide a neutral density ($\log_{10}$(radiation incident/radiation transmitted)) of at least about 0.3 (50% absorption) and preferably of about 1 (90% absorption) relative to the frequency distribution of the light radiation spectrum emitted by the flashlamp. For use with radiation weighted to the visible, black dyes such as Sudan black, are preferred light-absorption agents. Blue dyes, such as Nile blue, are also highly absorbing of flashlamp radiation. Red dyes are radiation-absorbing, but less so. It is found that UV-absorbing dyes, such as paranitrobenzoic acid (PABA), are far less efficient absorbers of flashlamp radiation, even when used with flashlamp radiation weighted to the UV, presumably because the distribution of absorption coefficients is not sufficiently broad to generate sufficient heat. In fact, it is found that PABA, which is "tanned" upon exposure to light radiation, becomes a more efficient producer of heat upon second and subsequent pulses of flashlamp radiation.

In order to most closely adjust the absorption of the light-absorption agent to the spectrum of the flashlamp, the light-absorption agent may comprise a mixture of several light-absorbing chemicals or dyes. The spectrum of the particular flashlamp, including the gas and the window may be predetermined, and from known absorption coefficients a mixture of dyes of appropriate concentrations may be formulated to closely correspond to the intensities of light radiation emitted at the various frequencies by the flashlamp. In order for a mixture of chemicals to be used as the light-absorption agent, it is generally necessary that they be soluble in a common solvent and nonreactive with each other when in solution.

The amount of light, and therefore the amount of heat produced, is both a function of the absorption coefficient distribution of the particular compound a mixture of compounds that comprise the agent and the amount that is applied to the surface. In the interest of minimizing the amount of material, therefore, it is preferred to use as dark (light-absorbing) an agent as possible. It is preferred that the agent have integrated absorption coefficients distributed at least about 50% in the visible spectrum, and preferably at least about 70% in the visible spectrum. Furthermore, it is desirable to minimize the amount of the light-absorption agent applied because energy is expended in vaporizing and/or decomposing the light-absorption agent from the surface itself. It is preferred that a neutral density of at least about 0.3 be achieved with a chemical that is distributed over a surface in an amount of about 5 kilograms per hectare or less and preferably in an amount of about 2 kilograms per hectare or less. For example, Sudan black provides a neutral density of about 1 when distributed over a surface in an amount of 2 kilograms per hectare.

The layer which is applied should be at least about 1-2 microns thick, and to generate sufficient localized heat, it is preferred that at least about 30 percent of the incident radiation be absorbed in a layer about 10 microns thick and more preferably that about 60 percent of the incident light radiation be absorbed in a layer about 10 microns thick.

Application of the light-absorption agent is generally crudely performed, e.g., by spraying a solution or dispersion of the light-absorption agent onto a surface or by premixing the agent with a chemical contaminant. The amount of agent which must be added per volume of solvent or carrier will depend on the nature of both the agent and of the solvent or carrier. However, generally between about 0.01 and about 0.1 gm of the agent will be dissolved in or dispersed in a liter of solvent or carrier.

In order to have any significant decontaminating effect, it is necessary that the flashlamp deliver a relatively intense dose of radiation. Some decontamination is generally evidenced when a prepared surface is exposed to about 6 joules per $cm^2$ of light energy. More substantial decontamination generally occurs when a prepared surface is exposed to about 10 joules per $cm^2$ of light energy. Because there is a removal of the light-absorbing chemical with each pulse, due to its vaporization and/or decomposition, the most substantial decontamination generally takes place with the first pulse. Accordingly, it is preferred that the pulses deliver at least about 10 joules per $cm^2$ of light energy to the material on the surface. In most cases there is little advantage to using pulses which deliver greater than about 20 joules per $cm^2$, and too high intensities may lead to overheating and surface deterioration.

It is generally preferred that a localized temperature of about 1000° C. be generated in a superficial 10 micron layer of surface material, and to achieve this, about 8000 joules of energy must be absorbed per $cm^3$ of surface material in this micron superficial layer. For example, assuming that 10 joules are delivered to the surface per $cm^2$ of surface area and that 50% of the light energy is absorbed in superficial 10 microns of material, including the dye and contaminant, in these 10 microns, about 5000 joules of energy will be absorbed per $cm^3$ of material, which energy will heat this surface layer to about 600° C.

Sometimes a single pulse is sufficient to adequately decontaminate a surface, and typically between one and five pulses are delivered to a contaminated surface area. In certain cases, up to about 10 or even up to about 15 pulses may be delivered; however, with each pulse, there is a reduction of the light-absorption agent. It is also contemplated that the light-absorption agent be reapplied to the surface between pulses; however, this depends on how thoroughly or how quickly the surfaces must be decontaminated.

Although in most situations the light-absorption agent will be administered to a surface subsequent to decontamination, in certain instances, the light-absorption agent will be admixed with the potential contaminant light-absorption agent in anticipation of surfaces becoming decontaminated therewith. This is particularly true of a chemical warfare agent, such as a defoliate, which is intended to be dispersed over a broad area, resulting in coverage of surfaces in that area. An army which disperses such an agent in a territory and eventually occupies the same territory will then need to decontaminate surfaces within the territory. By admixing a suitable light-absorbing dye or dyes with the chemical warfare agent, surfaces contaminated with the agent will also be prepared for decontamination by application of flashlamp radiation.

The light-absorption agent may be applied to a contaminated surface in a variety of manners so as to be in intimate contact with the contaminant. In most situations, the surface will carry a contaminant, and an operator removing the contaminant will apply the light-absorption agent to the surface. The light-absorption agent is typically dissolved in a suitable solvent, preferably a volatile solvent, and sprayed as an aerosol onto the surface. If the solvent is volatile, it is preferred to allow the solvent to vaporize. Next, an operator positions a flashlamp head closely adjacent to the surfaces of the object and actuates the apparatus to discharge one or more pulses of intense radiation pulses. The operator then repositions the flashlamp head adjacent to various areas of the surface until the entire surface is decontaminated.

Alternatively, the light-absorption agent might be dispersed in powder form onto a surface. The light-absorption agent might also be applied as a dispersion in a carrier liquid. If applied as powder or as a dispersion, it is preferred that the particulate size be less than about 1-2 microns to promote more even distribution of the light-absorption agent over the surface.

EXAMPLE

The invention will now be described in greater detail by way of the following study of decontamination of various surfaces contaminated with nerve compounds and nerve compound simulants.

Threat agents $C_2H_{16}PO_2F$ (GD), thickened GD (TGD), $C_4H_8Cl_2S$ (HD) and military chemical (EA 1699) were chosen for study. In addition the following substances were evaluated: 2-chloroethyl ethylsulfide (a HD simulant), diisopropylfluorophosphonate (a GD simulant) and bis (-ethylhexyl) hydrogenphosphite (a military (VX) simulant). The agents and simulants were applied to various surfaces both with and without dye, and subjected to different types, intensities, and numbers of UV pulses. The effect of the irradiation on compound degradation was evaluated by monitoring the compounds concentrates on the substrate before and after pulsing.

All experiments were performed in closed cells. The compounds of interest were placed on the appropriate surface and individually sealed in a cell with a retaining O-ring and synthetic quartz (Supracil). The O-ring separated the Supracil quartz window from the surface by approximately ¼ inch. All tests were run with neat agents and simulants. 2 μl of each contaminant was used in each case, which spread out to approximately 1 $cm^2$ of surface area.

After irradiation, the cell was disassembled, all interior surfaces were quickly rinsed with a solvent appropriate for the contaminant and the rinse solution was brought to volume in a volumetric flask. For each series of tests a contaminant control was obtained by sealing the contaminant in a cell, waiting a length of time equal to that required for irradiation, and analyzing the recovered nonirradiated sample. All further test results were normalized to the controls (blanks). That is, the recovery from the control cells was assigned a value of 100%, against which percent recovery from experimental cells was calculated, 0% recovery representing complete decontamination.

All analyses were performed according to procedures obtained from Edgewood Arsenal Quality Assurance Directorate. HD and the HD simulant were analyzed using the colorometric DB-3 method. Neat and thickened GD and its simulant were analyzed by the fluorometric procedures utilizing indole and sodium peroxide pyrophosphate. This method was also used for EA 1699 after conversion to the fluoride analog.

Utilizing parameters given in Table 1, preliminary tests were run using GD and HD.

TABLE 1

| EXPERIMENTAL PARAMETERS | |
| --- | --- |
| Agent volume used | 2 ul |
| Surface area covered | about 1 cm² |
| Distance (surface plane to flash lamp housing bottom) | 1.5" (3.8 cm) |
| Instrument voltage | 2.5 kV |
| Energy | 6 joules/cm, double pulse (high UV) |

The results are given in Table 2.

As seen from the Table 2 data, destruction of the agent appeared to be a function of the substrate. Highest destruction rates were observed for highly absorbent materials (black chloroprene, red silicon rubber). This observation led to the investigation of dyes absorbing in the visible range. Sudan Black was chosen for study.

For safety and ease of manipulation, simulants were chosen for the next series of tests. Experimental parameters were the same as set forth above in Table 1. Results of 2-chloroethylelthysulfide decontamination are set forth in Table 3.

TABLE 3

| | | 2-CHLOROETHYLETHYLSULFIDE | | |
| --- | --- | --- | --- | --- |
| TEST NUMBER | TOTAL NUMBER OF FLASHES | SURFACE | RECOVERY | COMMENTS AND OBSERVATIONS |
| 11 | 0 | Quartz | 100% | "Blank" all results normalized to this data point. |
| 12 | 5 | Quartz | 32% | No visible change after 1 shot, simulant spread out after 5. |
| 13 | 1 | Dye & Quartz | 11% | Approximately 0.1 mg Sudan Black dye sprinkled over the simulant. Much charring inside the cell. Smoke seen escaping from the cell, ash was difficult to remove from the surface even with solvent and rubbing. |

In these experiments approximately 0.1 mg of dye was sprinkled over the simulant. Although the disperision of dye was poor in this group, dramatic increases in decontamination were noted.

To study the effects of repeated decontamination on the representative surfaces, several drops of bis-ethylhexyl hydrogen phosphate with 0.14 dye were applied and run through many cycles in an open cell configuration. Observations appear in Table 4.

| TEST NUMBER | TOTAL NUMBER OF FLASHES | SURFACE | RECOVERY | COMMENTS AND OBSERVATIONS |
| --- | --- | --- | --- | --- |
| | | HD RESULTS | | |
| 1 | 0 | Quartz | 100% | Agent "blank", all results normalized to this point |
| 2 | 5 | Chloroprene | 11% | Whitish material observed through out cell after second flash. |
| 3 | 5 | Silicon Rubber | 8% | White material visible, much surface charring, soot throughout the cell. |
| 4 | 5 | Acrylic | 66% | No visible loss of agent. |
| | | GD RESULTS | | |
| 5 | 0 | Quartz | 100% | All results are normalized to this "blank" which duplicated experimental procedures without flashing |
| 6 | 1 | Quartz | 91% | |
| 7 | 3 | Quartz | 0% | This data point has low confidence, questionable transfer of agent. |
| 8 | 6 | Polycarbonate | 97% | Little change in agent drop. |
| 9 | 6 | Acrylic | 35% | Low confidence, questionable transfer. |
| 10 | 3 | Chloroprene | A 59% B 0% | Agent appeared to be ejected from plastic surface and distributed throughout the cell. "A" represents the recovery from the rest of the cell, excluding the plastic. "B" represents recovery from the plastic surface alone. |

TABLE 4
REPEATED DECON

| Test Number | | |
|---|---|---|
| 14 | Epoxy Polyamide | After 2 blasts completely charred surface. After 7 shots, not much change. |
| 15 | Acrylic | Surface appears to have been attacked as if by a solvent. Two shots - simulant/dye gone but surface appeared as though splattered with liquid. Surface slightly tacky, pitted, 15 shots total. |
| 16 | Silicon Rubber | One shot white on surface, VX sim appears to have soaked (dissolved in the rubber). Three shots liquid still visible, much charring - 15 shots total. |
| 17 | Polycarbonate | After 4 shots no apparent removal. Fifteen shots still liquid visible. |
| 18 | Black Chloroprene | Liquid still visible after 10 shots, 15 shots total liquid gone, surface charred but no real damage. |

Two μl of HD simulant was placed onto each of the representative surfaces, sealed in the cell, allowed to set for 30 minutes (no flashes) and then analyzed. Recovery shown in Table 5.

TABLE 5
30 MINUTE TEST

| TEST NUMBER | SURFACE | PERCENT RECOVERY BASED ON 30 MINUTE QUARTZ CONTROL |
|---|---|---|
| 19 | Quartz | 100% control |
| 20 | Acrylic | 77% |
| 21 | Polycarbonate | 13% |
| 22 | Silicon Rubber | 39% |
| 23 | Chloroprene | 94% |
| 24 | Epoxy Polyamide | 106% |

It was observed that the generation of a spectrum weighted to the UV by a double pulsing technique did not increase the decontamination appreciably. In order to obtain the maximum benefit of the visible light absorbing dye, it was decided to switch to a single pulse, increasing the visible output of the lamp as well as improving its lifetime. The unit was recalibrated for this operation to provide the following fluxes:

| Setting | Flux |
|---|---|
| 3.0 kV | 10 joules/cm |
| 2.5 kV | 7 joules/cm |
| 2.0 kV | 4 joules/cm |

To provide better distribution of the dye, techniques other than sprinkling were investigated. It was found that applying 0.1 mg of Sudan Black to the surface, adding a drop of ethanol to dissolve and disperse the dye and evaporating the solvent produced a uniform patch of dye, approximately 5 $cm^2$ in area. The dye was taken up easily by the simulants and agents and so this technique was used in all further work with dye.

In order to investigate the effects of various energy fluxes, the experiments were performed using diisopropyl fluorophosphonate. The results are shown in Table 6.

TABLE 6
DIISOPROPYL FLUOROPHOSPHONATE

| TEST NUMBER | SURFACE | NUMBER OF SHOTS | INSTRUMENT SETTING | ENERGY FLUX | PERCENT RECOVERY |
|---|---|---|---|---|---|
| 25 | Quartz | 2 | 30 kV | 10 joules/$cm^2$ | 66% |
| 26 | Quartz & Dye | 2 | 25 kV | 7 joules/$cm^2$ | 8% |
| 27 | Quartz & Dye | 3 | 25 kV | 7 joules/$cm^2$ | 3% |
| 28 | Quartz & Dye | 3 | 20 kV | 4 joules/$cm^2$ | 21% |

Based on these results, it was decided to perform all succeeding runs at 10 joules/$cm^2$. Verification of observed high levels of decontamination was performed with simulants before proceeding to agents. The following designations are used for brevity:

DFP - Diisopropyl Fluorophosphate
TDFP - DFP thickened with 3% Acryloid
SHD - Semi-mustard, 2-Chloroethyl Ethyl Sulfide
TSHD - Semi-mustard thickened with 3% Acryloid Results of tests run using these chemicals are shown in Table 7 below.

TABLE 7

| TEST NUMBER | SURFACE | SIMULANT | NUMBER OF SHOTS | PERCENT RECOVERY |
|---|---|---|---|---|
| 29 | Quartz | DFP | 0 | 100% (Control) |
| 30 | Quartz & Dye | DFP | 2 | 1% |
| 31 | Polycarbonate | DFP | 0 | 94% (Control) |
| 32 | Polycarbonate & Dye | DFP | 1 | 2% |
| 33 | Quartz & Dye | TDFP | 2 | 1% |
| 34 | Silicon Rubber | TDFP | 0 | 56% (Control) |
| 35 | Silicon Rubber | TDFP | 2 | 6% |
| 36 | Acrylic & Dye | TDFP | 2 | 4% |
| 37 | Polycarbonate & Dye | TDFP | 2 | <1% |
| 38 | Chloroprene & Dye | TDFP | 2 | <1% |
| 39 | Epoxypolyamide & Dye | TDFP | 2 | <1% |
| 40 | Quartz (No Dye) | TDFP | 2 | 40% |
| 41 | Quartz | TSHD | 0 | 100% (Control) |
| 42 | Quartz & Dye | TSHD | 2 | <1% |
| 43 | Quartz & Dye | SHD | 2 | <1% |
| 44 | Quartz (No Dye) | TSHD | 2 | 71% |

The high rates of decontamination observed in the simulant data above, indicates that a satisfactory set of parameters had been achieved. This work was verified using live agents. These results are given in Table 8 below.

TABLE 8

| TEST NUMBER | SURFACE | AGENT | NUMBER OF SHOTS | PERCENT RECOVERY |
|---|---|---|---|---|
| 45 | Quartz | GD | 0 | 100% (Control) |
| 46 | Quartz & Dye | GD | 2 | 3% |
| 47 | Quartz | HD | 2 | 100% (Control) |
| 48 | Quartz & Dye | HD | 2 | 4% |
| 49 | Quartz | EA 1699 | 0 | 100% (Control) |
| 50 | Quartz & Dye | EA 1699 | 2 | 14% |
| 51 | Polycarbonate & Dye | EA 1699 | 2 | 3% |
| 52 | Acrylic & Dye | EA 1699 | 2 | 6% |
| 53 | Quartz | Thickened GD | 0 | 100% (Control) |
| 54 | Quartz & Dye | TGD | 2 | 13% |
| 55 | Polycarbonate & Dye | TGD | 2 | 4% |

From this study, several observations can be made. Early experiments at 6 joules/cm$^2$, double pulse, using HD and GD threat agents, were mixed. Little decontamination was observed on non-absorbent surfaces. As much as 66% HD remained on acrylic after 5 flashes and 97% GD remained on polycarbonate after 6 flashes. Results on absorbent surfaces were much better. Only 8% HD remained on silicon rubber after 5 flashes and 0% GD was recovered from the surface of the chloroprene after 3 flashes. In the case of GD, large recoveries (50%) were observed on the top plate of the cell, indicating thermal ejection from the chloroprene. Based on this data, it was concluded that the main mechanism of decontamination appeared to be thermal, rather than molecular dissociation by direct UV absorption as originally thought. As the agents are rather poor absorbers in the visible and I.R. range, the use of a dye, Sudan Black, absorbing in this range was explored.

The effect of this visible radiation-absorbing dye is quite dramatic, as shown by tests 11–13. Five flashes without dye resulted in a 32% recovery, while 1 flash with dye produced an 11% recovery. After flashing, the dye appears to be almost entirely destroyed, with no "color" appearing in the analytical samples. A hard ash, apparently carbon, remains. The dye is quite soluble in all the agents, and tended to distribute itself throughout the droplet.

Surfaces, other than the epoxy polyamide, subjected to repeated decontamination showed minimal damage. In most cases, the surfaces were slightly charred on the surface with a light ash coating that was easily wiped off. The 1 mil thick film of epoxy polyamide was charred completely after only 2 flashes, although it retained a large portion of its tensile strength. It is not known how this substance would behave as a coating, as it was tested as a film sheet.

Table 5 shows the absorption of SHD on surfaces for 30 minutes. As seen, this absorption is quite dramatic on some surfaces. In some cases, excellent decontamination was observed on quartz, but was marginal on absorbent surfaces. In these cases, it is believed that unaffected simulant was extracted from the substrate after decontamination. Tests 29–40 demonstrated this effect. Non DFP-absorbing materials (chloroprene, epoxy polyamide, polycarbonate and quartz) showed excellent decontamination with less than 1% recovery. The absorbent materials, silicon rubber and acrylic showed 6% and 4% recovery, respectively. This did not seem to manifest itself in the live agent work.

Table 6 shows the effects of various fluxes. It appears that fluxes below 6 joules per cm$^2$ are not effective for decontamination, even with dye. The first flash, in all situations, appears to be the most important. If the pulse is not energetic enough, the material appears to be "distilled" or splattered throughout the cell. As the agent-/simulant then contains no dye, subsequent flashes appear to have little effect. This effect is verified by the acoustic report of each flash. The cell exhibited explosive venting through distention of the O-ring. When complete decomposition occurs, one would expect the volume of gas to be many times greater than that created by simple volatilization of the agent. With HD as an example:

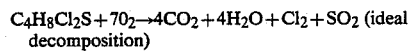
$$C_4H_8Cl_2S + 7O_2 \rightarrow 4CO_2 + 4H_2O + Cl_2 + SO_2 \text{ (ideal decomposition)}$$

In this case the volume of decomposition products would be ten times that of the volatilized agent. This manifests itself in a much louder report when decomposition occurs. In most cases, a very loud report was observed with the first flash. Subsequent flashes produced much softer reports. The initial report also gives a good indication of the amount of decontamination found by chemical analysis.

Table 8 verifies the simulant data from live agents. Results for HD and GD were quite good with greater than 95% decontamination achieved with 2 flashes. The less volatile agents, TGD and EA 1699, also did quite well on acrylic and polycarbonate, but had trouble on quartz. It appeared that the agent had recondensed, with TGD found on the top plate and EA 1699 found on the bottom. The TGD was much more viscous than the TDFP. This, along with the much lower volatility of the agents suggests a possible explanation for the discrepancy between the simulant and agent data.

Several advantages of the present invention can now be more fully appreciated. The present invention provides a method for decontaminating surfaces for which no practical decontamination procedure presently exists. Flashlamp apparatus is readily transportable to remote locations where decontamination is required, and the flashlamp heads, weighing only a few pounds, can be easily moved across a surface. The application of a light-absorbing dye to the surface provides that the heat is concentrated at the contaminant rather than at the surface itself, whereby the surface is relatively unaffected by the heat and is protected from heat effects by vaporization of the light-absorbing dye and contaminant and their decomposition products. The dye also indicates removal of the contaminant from the surface and indicates whether contaminant droplets have resettled on the surface. Decontamination is very rapid, and therefore, the method is very applicable to removing chemical warfare agents from surfaces. Indications are that most of the contaminant is decomposed, whereby the removed contaminant does not represent a continuing contamination problem.

Although the decontamination is shown to be primarily a thermal effect, rather than a photochemical effect, the light radiation does contribute somewhat to decomposition of the vaporized chemicals. In this regard, the polychromatic light produced by flashlamps is advantageous relative to monochromatic light produced by lasers. Monochromatic light tends to break only those chemical bonds which are activated by wavelengths of the particular frequency. The breaking of particular bonds in certain toxic chemicals that may occur when exposed to monochromatic light, may produce daughter chemicals which are also toxic. Broad-band radiation, on the other hand, is expected to photochemically decompose a wider range of chemical bonds and to fragment the contaminant into more elementary units, which are less likely to be toxic.

While the invention has been described in terms of certain preferred embodiments, modifications obvious to one with ordinary skill in the art may be made without departing from the scope of the present invention.

Various features of the invention are set forth in the following claims.

What is claimed is:

1. A method of destroying a chemical warfare agent, pesticide or other hazardous organic chemical contaminant on a surface to be decontaminated comprising the steps of positioning a pulsed light flashlamp system in proximity to the surface to be decontaminated, said pulsed light flashlamp system providing high intensity light pulses over a wide surface area having a light radiation spectrum having a broad-band frequency distribution such that at least about 50 percent of the light energy thereof is distributed in the visible spectrum between 380 and 720 nanometers of wavelength and having a duration of less than about 10 milliseconds, intimately contacting said contaminant with a high optical density visible spectrum light-absorption agent that absorbs broad-band frequency light radiation in an amount sufficient to provide a neutral density of about 0.3 or greater relative to said light radiation spectrum, said agent being distributed over said surface at a level of about 5 Kg per hectare or less, and exposing said surface to be decontaminated to at least one pulse of high intensity broad-band incoherent light from said flashlamp system at an intensity of at least about 6 joules per square centimeter at said surface to be contaminated such that said agent absorbs at least 50 percent of the energy of said at least one broad-band light pulse for said light-absorption agent to generate sufficient heat at a temperature of at least about 1000° C. to vaporize and decompose said hazardous organic chemical contaminant from the surface without substantially redispersing said contaminant, whereby said surface is at least partially shielded from said at least one light pulse by said absorption such that deterioration of said surface is avoided or minimized.

2. A method according to claim 1 wherein said light-absorption agent is applied to a surface in an amount sufficient to provide a neutral density of about 1.0 or greater relative to the light radiation of the flashlamp.

3. A method in accordance with claim 1 wherein said flashlamp is powered and placed in sufficient proximity to the contaminated surface so that each pulse delivers at least about 10 joules of broad-band light energy per $cm^2$ of surface area of said contaminated surface.

4. A method in accordance with claim 1 wherein said flashlamp system produces radiation of frequencies extending throughout the visible range, at least about 70% of its light energy being in the visible range.

5. A method according to claim 1 wherein said high density broad-band visible light absorption agent has an integrated distribution of absorption coefficients at least about 50% distributed in the visible range.

6. A method according to claim 1 wherein said high density broad-band visible light absorption agent has an integrated distribution of absorption coefficients at least about 70% distributed in the visible range.

7. A method in accordance with claim 1 wherein said pulse is delivered in a period of about 1 millisecond.

8. A method in accordance with claim 1 wherein said high density broad-band visible light absorption agent is Sudan Black or Nile Blue.

9. A method in accordance with claim 1 wherein said high optical density broad-band absorption agent is applied to said comtaminant by dissolving said agent in a solvent to provide a dilute solution of the agent and applying the resulting dilute solution to the contaminant surface.

10. A method in accordance with claim 9 wherein said agent is present in said dilute solution at a concentration in the range of from about 0.01 to about 0.1 gram per liter of said solution.

11. A method in accordance with claim 1 wherein said high optical density broad-band absorption agent is applied to said contaminated surface by preblending with said contaminant.

* * * * *

UNITED STATES PATENT AND TRADEMARK OFFICE
CERTIFICATE OF CORRECTION

PATENT NO. : 4,867,796

DATED : September 19, 1989

INVENTOR(S) : Asmus, et al.

It is certified that error appears in the above-identified patent and that said Letters Patent is hereby corrected as shown below:

In column 6, line 50, after the word "light" insert the word --absorption--.

In column 6, line 52, after the word "compound" insert the word --and--.

In column 8, line 47, change the word "compounds" to the word --compound--.

In columns 9-10, in Table 2, lines 6 and 7, change the words "through out" to the word --throughout--.

In columns 9-10, in Table 2, line 15, after the word "flashing" insert a period --.--.

In column 14, line 28, change "$70_2$" to read --$7O_2$--.

In column 11, line 27, after the word "Recovery" insert the word --is--.

In column 12, line 21, change "$cm^2in$" to read --$cm^2$ in--.

UNITED STATES PATENT AND TRADEMARK OFFICE
CERTIFICATE OF CORRECTION

PATENT NO.   : 4,867,796
DATED        : September 19, 1989
INVENTOR(S)  : Asmus, et al.

It is certified that error appears in the above-identified patent and that said Letters Patent is hereby corrected as shown below:

In column 16, line 6, Claim 1, after the words "chemical contaminant" insert --and thereby remove substantially all of said contaminant--.

Signed and Sealed this

Sixteenth Day of March, 1993

Attest:

STEPHEN G. KUNIN

Attesting Officer

Acting Commissioner of Patents and Trademarks